United States Patent
Karladani

(12) 
(10) Patent No.: US 6,206,880 B1
(45) Date of Patent: Mar. 27, 2001

(54) METHOD FOR PERCUTANEOUS INTRAMEDULLARY NAILING OF TIBIAL SHAFT FRACTURES

(76) Inventor: Abbas Karladani, 444 96 Ödsmål, Pojkebo (SE)

( * ) Notice: Subject to any disclaimer, the term of this patent is extended or adjusted under 35 U.S.C. 154(b) by 0 days.

(21) Appl. No.: 09/511,129

(22) Filed: Feb. 21, 2000

(51) Int. Cl.$^7$ .................................................. A61B 17/72
(52) U.S. Cl. ................................ 606/62; 606/88; 606/104
(58) Field of Search .................................. 606/62, 63, 64, 606/67, 60, 72, 75, 86, 88, 99, 104, 185; 128/898

(56) References Cited

U.S. PATENT DOCUMENTS

| | | | |
|---|---|---|---|
| 5,374,271 | * | 12/1994 | Hwang ..................................... 606/86 |
| 5,490,852 | * | 2/1996 | Azer et al. .............................. 606/79 |

* cited by examiner

*Primary Examiner*—David O. Reip
(74) *Attorney, Agent, or Firm*—Samuels, Gauthier & Stevens, LLP

(57) ABSTRACT

A method for percutaneous intramedullary nailing of tibial shaft fractures, intended to prevent anterior knee pain, comprising: placing a patient having at least one injured leg (1) in a supine position on a traction table; adjusting the leg so that the knee joint is flexed to approximately 90° at a joint line (J); preparing and draping the leg; making an incision (6, 6') adjacently to the patella (4); creating a tunnel behind a patellar tendon of the injured leg, by means of a first tool, in a direction towards a tibial cortex of a tibia of the injured leg; penetrating the tibial cortex with a second tool; penetrating through the tibial cortex further into a medullary channel of the tibia (2) with a third tool; inserting an intramedullary nail into the medullary channel through the incision (6, 6'), wherein the incision (6, 6') is made medially or laterally to the patella (4) and perpendicularly to the joint line (J).

10 Claims, 1 Drawing Sheet

METHOD FOR PERCUTANEOUS INTRAMEDULLARY NAILING OF TIBIAL SHAFT FRACTURES

TECHNICAL FIELD

The present invention relates to a new method of surgery approach for percutaneous intramedullary nailing of tibial shaft fractures, intended to prevent anterior knee pain.

BACKGROUND OF THE INVENTION

It is previously known to insert intramedullary nails into human skeletal bones e.g. when treating and fixating bone fractures, or correcting bone malalignments.

In numerous studies, intramedullary nailing has proved to be an effective and safe treatment for closed and grade I, II and IIIa open tibial shaft fractures. Intramedullary nailing has also been reported to be comparable to external fixation for treatment of grade IIIb open fractures.

The techniques and devices for intramedullary nailing have been improved, so that the time to union, the rate of infections, and the general function of the patient today are superior in comparison to other conventional treatment methods.

However, in the literature it has frequently been reported that patients can perceive anterior knee pain after the insertion of an intramedullary nail. Such anterior knee pain is a troublesome complication, which is especially painful when the patient is kneeling down. Therefore, it arises that patients in professions which require the use of such body positions are permanently disabled after the insertion of an intramedullary nail.

It has been found that nail insertion through the tendon more often results in anterior knee pain than if paratendinous insertion is used.

The etiology to the complication with anterior knee pain, however, is not clearly defined in the literature. Some authors have stated that the reason for the anterior knee pain is that an injured infrapatellar nerve produces a neuroma which causes the pain sensation. Others have claimed that the high position of the nail in relation to the anterior cortex and the tibial plateau are the reasons for the complication.

In a study by Hooper et al. (1991), concerns for the problem with anterior knee pain are expressed.

Furthermore, according to a study of Orfaly et al. (1995), 61 out of 107 patients (56%) developed troublesome knee pain in the area of nail insertion. When a paratendinous insertion was used, 33 out of 65 fractures (51%) were associated with subsequent knee pain. When nail insertion was performed through the tendon, 28 out of 36 knees (78%) developed subsequent pain. Orfaly et al. concluded that the nail position in relation to the anterior cortex and tibial plateau had no influence on the occurrence of knee pain, and that the response to nail removal was unpredictable.

Some authors, e.g. Zucman and Maurer (1970) recommend a longitudinal midline incision.

However, according to Court-Brown et al., a longitudinal midline incision might result in cutaneous nerve damage and significant keloid formation. Therefore, Court-Brown et al. propose the use of a transverse incision of approximately 3" (8 cm), which is made midway between the joint line and the tibial tubercle.

Mochida et al. studied the anatomic distribution of the infrapatellar branch of the saphenous nerve in cadavers, and investigated the incidence of injury to this branch in 68 patients after arthroscopic knee surgery. It was found that the safe incision area was within an area extending approximately 30 mm from the medial margin of the patella at the level of the midpatella, and within an area extending approximately 10 mm from the medial margin of the patella ligament at the level of the distal pole of the patella. In 30% of the examined cadavers it was found that the infrapatellar branch of the saphenous nerve extended transversely in a lateral direction before it crossed the proximal edge of the tibia.

Furthermore, it was found that the infrapatellar nerve extended at an angle of 45 degrees towards the articular surface of the tibia when the joint was extended, and almost horizontally and parallel to the articular surface when the joint was flexed 90 degrees.

In spite of the findings of the above-mentioned authors, there is still a need for a new method for percutaneous intramedullary nailing of tibial shaft fractures which reduces, and preferably eliminates the problem with anterior knee pain.

It is the belief of the present inventor that possible etiologies for anterior knee pain as a result of the previously known treatment methods include injury to the infrapatellar nerve and/or iatrogenic trauma to, or dissection around, the patellar tendon.

SUMMARY OF THE INVENTION

It is therefore a first object of the present invention to provide a method for percutaneous intramedullary nailing of tibial shaft fractures, which does not harm the infrapatellar nerve, and which also prevents neuroma formation and avoids gliding tissue and direct trauma and dissection around the patellar tendon.

In accordance with claim 1, the first object of the present invention is achieved by means of a method comprising the steps of: placing a patient on a traction or fracture table; placing an injured leg of the patient so that a knee joint of the injured leg is flexed to approximately 90° at a joint line; preparing the skin of the injured leg within an intended incision region and draping regions of the injured leg surrounding the incision region; making an incision adjacently to a patella of the injured leg; creating a tunnel behind a patellar tendon of the injured leg, by means of a first tool, in a direction towards a tibial cortex of a tibia of said injured leg; penetrating the tibial cortex with a second tool and removing the second tool; penetrating through the tibial cortex further into a medullary channel of the tibia with a third tool and removing the third tool; inserting an intramedullary nail into the medullary channel through the incision.

Thereby, according to the invention, the incision is made medially or laterally to the patella and perpendicularly to the joint line.

Further objects of the present invention will become evident from the following description, wherein the features which makes it possible to achieve the further objects are defined in the appended dependent claims.

BRIEF DESCRIPTION OF THE DRAWINGS

In the following, the present invention will be described in greater detail with reference to the attached drawings, in which FIG. 1 schematically depicts a portion of an injured leg of a patient, wherein some of the skeletal bones are indicated with dashed lines.

DETAILED DESCRIPTION OF PREFERRED EMBODIMENT

Figure 1:
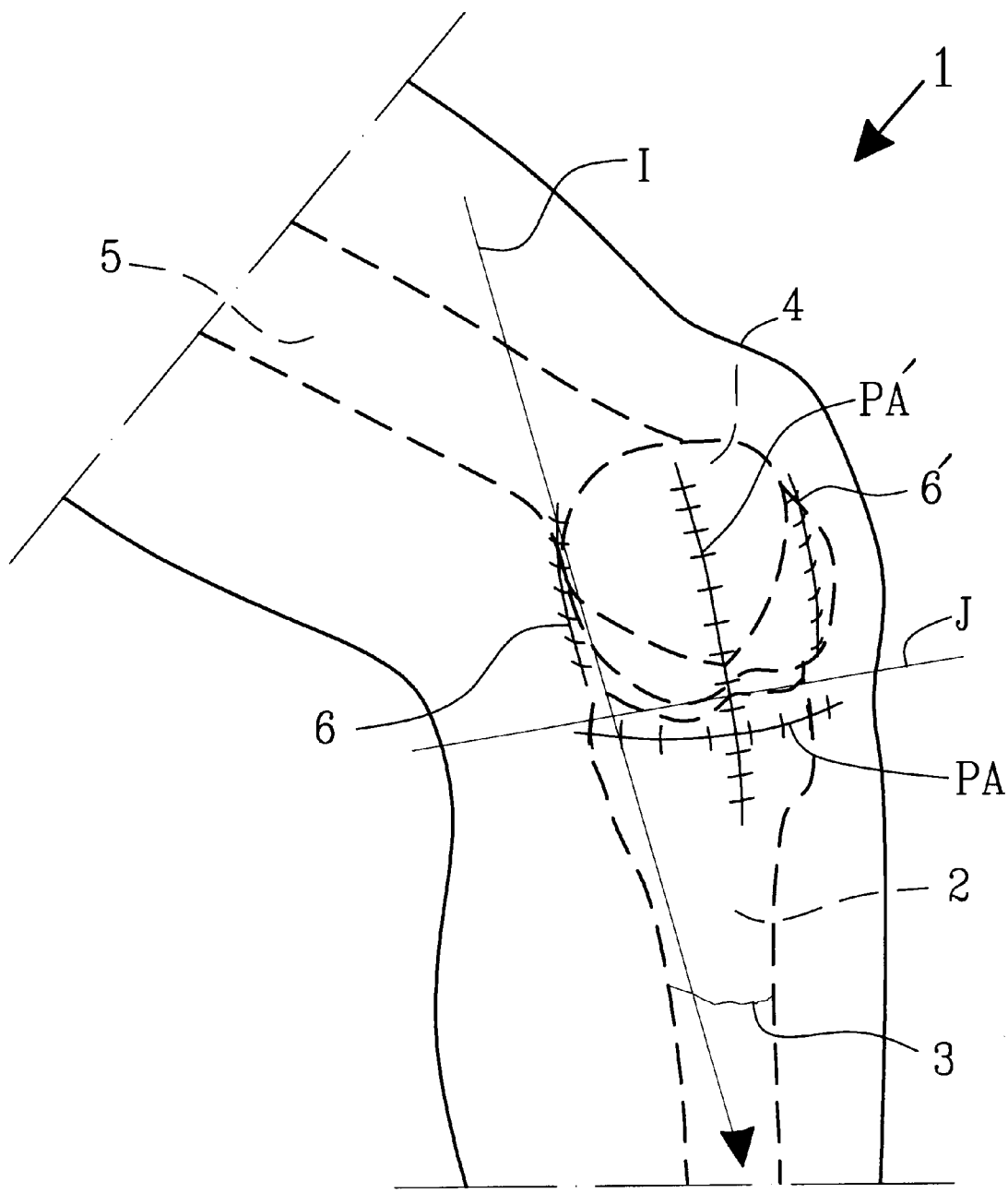

In the following, a preferred embodiment of the method according to the invention will be described, and when applicable with reference to the attached FIG. 1.

FIG. 1 shows a portion of an injured left leg 1, seen diagonally in relation to the medial, wherein the tibia 2 (i.e. the tibia shaft), indicated with dashed lines, has a fracture 3. Furthermore, in FIG. 1, the patella 4 and the femur 5 also have been indicated with dashed lines. Accordingly, only the skeletal bones which are necessary in order to understand the invention have been indicated in FIG. 1.

According to the invention, in a first step a patient having at least one injured leg 1, i.e. a fractured tibia, is placed on a traction or fracture table (not shown in FIG. 1), conveniently in a supine position. Thereafter, if possible (i.e. in case the patient has two legs), the uninjured leg of the patient is secured in an abducted position with the knee and hip joints in their natural positions (not shown in FIG. 1). In the next step, the injured leg of the patient is placed so that the knee joint of the injured leg is flexed to approximately 90° at a joint line. After this the skin of the injured leg is prepared within the intended incision region, wherein the regions surrounding the intended incision region are draped.

Thereafter, according to the invention, an incision 6 which preferably is 2.5–4,5 cm long is made medially or laterally to the patella 4. According to the invention, the incision 6 is placed perpendicularly to the joint line J.

In the previously known methods for inserting intramedullary nails into human skeletal bones, the incision would instead be made approximately parallel and distal to the joint line, as indicated by the line PA in FIG. 1, or longitudinally from the tibia tuberosity (ending distal to the joint line) as indicated by the PA' in FIG. 1.

According to the invention, the incision 6 preferably extends from the superior edge of the patella to the level of the inferior patellar edge, along one lateral side of the patella. Even more advantageously, the incision ends above the inferior edge to the patella.

In a preferred embodiment of the method according to the invention, the incision is made in a way avoiding all dissection around lateral and medial edges of the patellar tendon of in injured leg.

According to the invention, the medial or lateral retinaculum (not visible in FIG. 1) will preferably be incised about 5 mm from its junction to the patella, along the skin incision 6, in a way creating a tunnel behind the patellar tendon of the injured leg. As is indicated in FIG. 1, it is conceivable to have incisions 6, 6' on either side of the patella 4.

After the incision 6, dissection is carried out with, preferably, a pair of mayo scissors between the retinaculum and the joint capsule (not visible in FIG. 1), in a direction towards the tibial cortex (not visible) just above the tibial tuberosity. An appropriate place for nail insertion is identified, and an erected awl is used to penetrate the tibial cortex. Thereafter, the erected bone awl is substituted with an AO bone awl which penetrates further into the medullary channel in an appropriate direction. If necessary, a guide wire is passed down into the distal tibia 2.

After the above-described preparations, an appropriate intramedullary nail (not shown in FIG. 1) is inserted in a manner specified by the manufacturer in question. In FIG. 1, the arrow I indicates one of the possible insertion directions for the intramedullary nail through the incision 6.

It should be understood that the present invention by no means should be regarded as being limited to what has been described in the foregoing description, or to the features shown in the attached drawing, and that the scope of the invention if defined by the appended claims.

What is claimed is:

1. A method for percutaneous intramedullary nailing of tibial shaft fractures, comprising the steps of:

placing a patient on a traction or fracture table;

placing an injured leg of said patient so that a knee joint of said injured leg is flexed approximately 90° at a joint line;

preparing the skin of said injured leg within an intended incision region and draping regions of said injured leg surrounding said incision region;

making an incision adjacently to a patella of said injured leg;

creating a tunnel behind a patellar tendon of said injured leg, by means of a first tool, in a direction towards a tibial cortex of a tibia of said injured leg;

penetrating said tibial cortex with a second tool and removing said second tool;

penetrating through said tibial cortex further into a medullary channel of said tibia with a third tool and removing said third tool;

inserting an intramedullary nail into said medullary channel through said incision; wherein the incision is made medially or laterally to said patella and perpendicularly to said joint line.

2. A method according to claim 1, wherein the incision extends between 2.5–4,5 cm from a superior to an inferior edge of said patella along one lateral side of said patella.

3. A method according to claim 1, wherein the incision ends above said inferior edge of said patella.

4. A method according to claim 1, wherein the incision is made in a way avoiding all dissection around lateral and medial edges of a patellar tendon of said injured leg.

5. A method according to claim 1, wherein a medial or lateral retinaculum of said knee joint is incised in a way creating a tunnel behind said patellar tendon of said injured leg.

6. A method according to claim 1, wherein the step of creating a tunnel is carried out between a medial or lateral retinaculum and a joint capsule of said knee joint in a direction towards said tibial cortex just above a tibial tuberosita of said tibia.

7. A method according to claim 1, wherein the first tool is a pair of mayo scissors.

8. A method according to claim 1, wherein the second tool is an erected awl.

9. A method according to claim 1, wherein the third tool is an AO bone awl.

10. A method according to claim 1, wherein a guide wire is passed down into a distal end of said tibia before said intramedullary nail is inserted.

* * * * *